United States Patent [19]

Cleary

[11] Patent Number: 4,950,157

[45] Date of Patent: Aug. 21, 1990

[54] DEBONDING INSTRUMENT FOR ORTHODONTIC BRACKETS

[75] Inventor: James D. Cleary, Glendora, Calif.

[73] Assignee: Unitek Corporation, Monrovia, Calif.

[21] Appl. No.: 270,522

[22] Filed: Nov. 14, 1988

[51] Int. Cl.$^5$ ............................................. A61C 3/00
[52] U.S. Cl. ...................................................... 433/4
[58] Field of Search ...................... 433/159, 160, 3, 4

[56] References Cited

U.S. PATENT DOCUMENTS 4,553,932  11/1985  Armstrong et al. ..................... 433/4
4,776,791  10/1988  Hannula ................................. 433/4

FOREIGN PATENT DOCUMENTS 323504  12/1934  Italy ..................................... 433/159

OTHER PUBLICATIONS

Pg. 1–4, Orthodontic Catalog No. 122 of United Corp., Monrovia, CA (©1989).

Primary Examiner—Cary E. Stone
Attorney, Agent, or Firm—Donald M. Sell; Walter N. Kirn; James D. Christoff

[57] ABSTRACT

An adjustable orthodontic debonding instrument has jaws that may be opened to place jaw tips over mesial and distal sides of the bracket, and then closed to enhance the grip of the jaws on the bracket sides. An actuator is moveable along the length of a handle of the instrument, and cooperates with a lever arm fixed to the moveable jaw to facilitate precise movement of the latter and enhance the grip of the jaws on the bracket when the jaws are closed. A slight, quick pivotal movement of the instrument handle by the user presents a torsional force to the bracket base which is particularly advantageous when debonding ceramic orthodontic brackets.

10 Claims, 1 Drawing Sheet

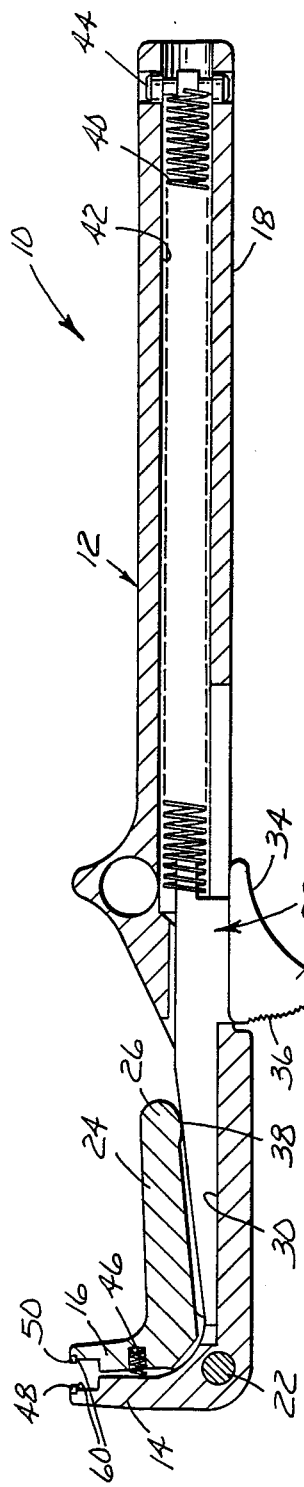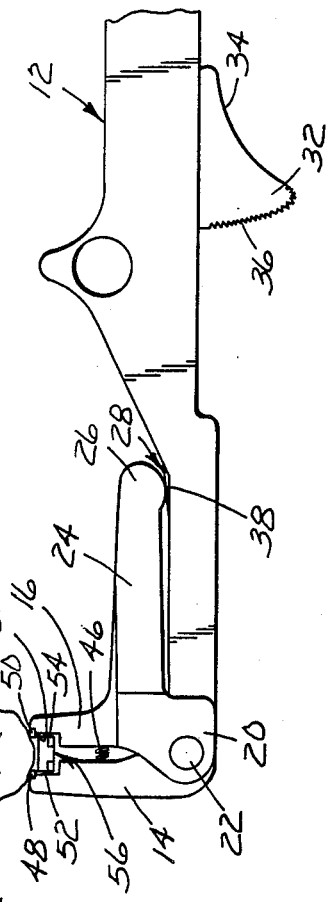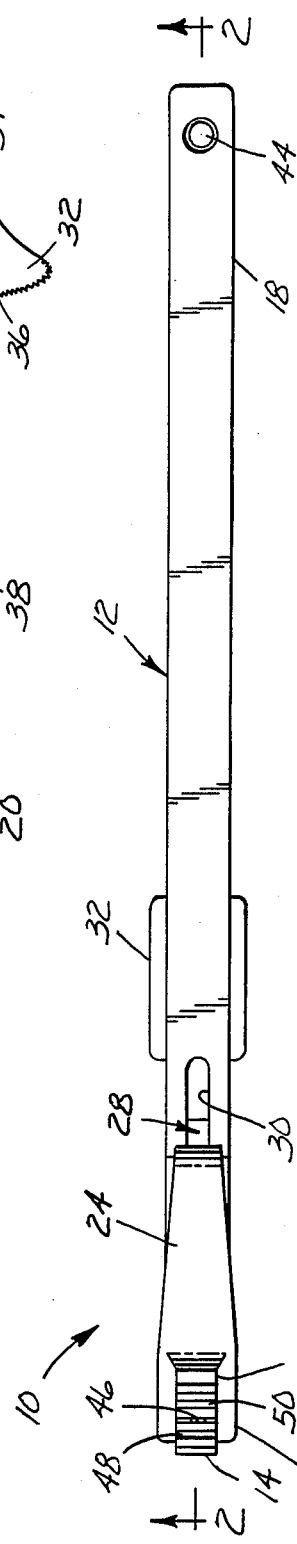

DEBONDING INSTRUMENT FOR ORTHODONTIC BRACKETS

BACKGROUND OF THE INVENTION

1. Field of the Invention

This invention relates to an adjustable orthodontic hand tool for removing orthodontic brackets from teeth.

2. Description of the Related art

The removal of orthodontic brackets from the mouth following the active phases of treatment poses special considerations in instances where the brackets are adhesively mounted directly on the teeth. Stainless steel brackets, for example, are often debonded by a tool which utilizes a peeling motion to fracture the junction between the bracket base and the adhesive.

Orthodontic brackets made from ceramic materials, however, do not bend and may fracture when subjected to a peeling action, thereby rendering complete removal of the bracket difficult and time consuming. In response to this problem, an inexpensive tool has been developed which, when placed over the bracket, is manipulable to exert a torsional motion to the bracket and break the bond interface between the base of the bracket and the adhesive. This tool has a pair of fixed, rigid jaws that are spaced apart from each other a constant distance slightly greater than the mesial-distal width of the bracket, with an elongated handle of the tool extending away from the mouth in a direction somewhat parallel to the occlusal plane and perpendicular to the tool jaws.

The necessary clearance between the bracket and the fixed jaws of conventional debonding tools cannot be realistically reduced below a certain minimum value without hampering the ability of the orthodontist to properly position the jaws over the bracket sides, even though the effectiveness of the grip of the jaws on the bracket is compromised as a result of the clearance. Moreover, the fixed jaws cannot accommodate brackets of differing widths.

SUMMARY OF THE INVENTION

In accordance with the invention, an instrument for removing orthodontic brackets from teeth includes an elongated frame having a handle portion, a first jaw connected to the frame, a second jaw, and means coupling the second jaw to the frame for movement of the second jaw either toward or away from the first jaw. In addition, the instrument includes means yieldably biasing the second jaw toward the first jaw, and a manually operable actuator connected to the frame for selective movement relative to the frame. The actuator is operable to shift the second jaw toward the first jaw during movement of the actuator in a direction generally along the length of the frame.

As a consequence, the jaws of the instrument can be precisely adjusted to tightly grip orthodontic brackets of differing widths, and the instrument thereafter manipulated to debond each bracket from an associated tooth without a substantial likelihood of fracturing the bracket or dropping the bracket within the mouth subsequent to debonding. The tool is adapted for compact construction and one-handed operation, and thus facilitates the orthodontist's vision of the debonding operation.

BRIEF DESCRIPTION OF THE DRAWINGS

FIG. 1 is a front elevational view of a debonding instrument of the present invention;

FIG. 2 is a sectional view of the instrument taken along line 2—2 of FIG. 1; and FIG. 3 is a fragmentary, plan view somewhat similar to FIG. 2 except that an activator of the instrument has been shifted rearwardly to open a pair of jaws in order to grasp opposite sides of a bracket mounted on a tooth.

DESCRIPTION OF THE PREFERRED EMBODIMENT

An orthodontic instrument 10 for removing orthodontic brackets from teeth and constructed in accordance with a preferred embodiment of the invention is illustrated in FIGS. 1–3 and includes a frame 12, a first jaw 14 and a second jaw 16. The frame 12 is elongated and integrally connected to the first jaw 14 in such a manner that the frame 12 and the first jaw 14 present a generally L-shaped overall configuration. The frame 12 includes a handle portion 18 remote from the first jaw 14.

The second jaw 16 is formed to present a bifurcated hinge section 20 that straddles a portion of the frame 12. A pin 22 represents a pivot means coupling the hinge section 20 of the second jaw 16 to the frame 12 for movement of the second jaw 16 either toward or away from the first jaw 14. The second jaw 16 also includes an integral lever arm 24 that extends in a direction generally along the length of the frame 12, and the lever arm 24 terminates in a free end portion 26 remote from the pin 22.

An elongated actuator 28 is received in a channel 30 formed in the frame 12 and is moveable relative to the frame 12 in either direction along the longitudinal axis of the latter. An enlarged thumb button 32 of the actuator 28 protrudes outwardly from the channel 30 in a direction transverse to the length of the frame 12, and the button 32 includes a concave rear portion 34 as well as a knurled forward portion 36.

A front section of the actuator 28 is disposed alongside the lever arm 24 and includes a camming edge portion 38 that extends at an acute angle relative to the longitudinal axis of the frame 12. The free end portion 26 has a transverse, front-to-back, horizontal thickness (in a direction parallel to the longitudinal axes of jaws 14, 16) that is somewhat wider than adjacent regions of the lever arm 24 and rests in sliding contact against the camming edge portion 38.

A first compression spring 40 is received in a bore 42 that extends internally along the length of the frame 12, and a forward region of the spring 40 is received around a rearwardly extending projection of the actuator 28 with the front of the spring 40 bearing against an adjacent shoulder of the actuator 28. A rearward end of the spring 40 is in contact with a pin 44 that is pressed into a transverse hole formed in the frame 12.

A second compression spring 46 is disposed within a small, internal bore formed in the second jaw 16, and includes a front protruding portion that is in contact with an inside wall of the first jaw 14. The second spring 46 yieldably biases the second jaw 16 away from the first jaw 14 and retains the free end portion 26 of the lever arm 24 in contact with the camming edge portion 38 of the actuator 28.

The first spring 40 has a spring force sufficient to overcome the combined effects of the spring force exhibited by the second spring 46 and the torque presented by the lever arm 24. Consequently, whenever the user disengages the thumb button 32, the first spring 40 is operable to shift the actuator 28 in a forward direction along the length of the frame 12 and cause the free end portion 26 to ride up the camming edge portion 38, thereby pivoting the second jaw 16 in a counterclockwise direction viewing FIG. 2 and enable a relatively hard, protruding, flat-edged tip 50 of the second jaw 16 to move toward a similar protruding tip 48 of the first jaw 14 against the bias presented by the second spring 46. To open the jaws 14, 16, the actuator 28 is shifted rearwardly by thumb pressure on the forward portion 36 of the thumb button 32 against the force presented by the first spring 40, thus permitting the second spring 46 to pivot the second jaw 16 in a clockwise direction viewing FIG. 2 and open the jaws 14, 16 as the free end portion 26 rides down the camming edge portion 38.

In use, the thumb button 32 is first moved toward the rear of the frame 12 to open the jaws 14, 16, and the instrument 10 is then placed adjacent the mouth with the handle 18 extending in a direction generally parallel to the occlusal plane of the patient. The user continues to hold the thumb button 32 in a rearwardly oriented direction as the working tips 48, 50 of the jaws 14, 16 are moved closely adjacent mesial and distal sides 52, 54 of a bracket 56 mounted on a tooth 58.

Once the tips 48, 50 of the instrument 10 are properly aligned with the bracket 56 in an occlusal-gingival direction and the tips 48, 50 are next to the base of the bracket 56, thumb pressure is released from the button 32 and the tips 48, 50 move toward a position of firm contact with the bracket sides 52, 54. A recess 60 behind each of the tips 48, 50 ensures flat engagement of the tips 48, 50 with the respective bracket side 52, 54. The first spring 40 is of sufficient strength to thereafter retain the tips 48, 50 in firm engagement with the bracket sides 52, 54 during the debonding operation, although if desIred the end of the practitioner's thumb may be shifted to press against the rear portion 34 of the button 32 in order to increase the pressure of the grip exerted by the jaws 14, 16 on the bracket 56.

Next, the handle 18 is slightly rotated with a quick, snap movement to pivot the instrument 10 about an axis that is generally perpendicular to the base of the bracket 56. The torsional shear motion presented by the tips 48, 50 on the bracket 56 breaks the bond interface between the surface of the tooth 58 and the adhesive, so that only a minor effort afterwards is necessary to clean the tooth surfaces.

After the debonding operation, the first spring 40 maintains the jaws 14, 16 in firm contact with the bracket 56 whether or not thumb pressure is exerted on the rear portion 34 of the button 32, so that there is little likelihood that the debonded bracket 56 will unintentionally disengage the jaws 14, 16 and fall into the patient's mouth. However, as soon as the jaws 14, 16 are removed from the mouth area, pressure on the forward portion 36 by the user to shift the actuator 28 in a rearwardly direction causes the jaws 14, 16 to open and enable the bracket 56 to freely fall into a waste receptacle.

Preferably, the jaw tips 48, 50 are formed from or coated with a material such as carbide or ceramic which is of a hardness similar to or exceeding the hardness of the aluminum oxide material forming the bracket 56. Additionally, it is preferable that the tips 48, 50 are relatively narrow in a direction toward the pin 22 so that the torsional debonding force is presented primarily to regions adjacent the base of the bracket 56. As a result, the probability is increased that the bracket 56 will not fracture and that instead only the adhesive junction will be broken.

The construction of the instrument 10 is particularly advantageous in that the yoke-shaped hinge section 20 in cooperation with the frame 12 is compact yet strong enough to resist the relatively large torsional forces exerted during the debonding operation. Moreover, provision of the lever arm 2 facilitates retention of the jaws 14, 16 in a closed position during the debonding operation and also enables the practitioner to precisely shift the second jaw 16 only a slight distance even though the thumb button 32 is moved, by comparison, to a much greater extent. Yet, the instrument 10 presents a relatively small profile and is readily usable within the confines of the mouth while permitting the practitioner to clearly observe placement of the tool and the subsequent debonding operation.

I claim:
1. An instrument for removing orthodontic brackets from teeth comprising:
   an elongated frame including a handle portion;
   a first jaw connected to said frame and having a tip with a generally flat edge for gripping a side of an orthodontic bracket;
   a second jaw having a tip with a generally flat edge opposed to said edge of said first jaw for gripping an opposite side of the bracket;
   means coupling said second jaw to said frame for movement of said second jaw either toward or away from said first jaw;
   means yieldably biasing said second jaw toward said first jaw; and
   a manually operable actuator movably connected to said frame, said actuator being operable to shift said second jaw toward first jaw during movement of said actuator in a direction generally along the length of said frame.
2. The instrument of claim 1, wherein said second jaw includes a lever arm extending in a direction generally parallel to the longitudinal axis of said frame, said lever arm including a free end portion in contact with said actuator.
3. The instrument of claim 2, wherein said free end portion is in sliding contact with said actuator.
4. The instrument of claim 3, wherein said actuator includes a camming edge portion extending at an acute angle relative to the longitudinal axis of said frame, said camming edge portion being in sliding contact with said actuator.
5. The instrument of claim 1, wherein said first jaw is fixed relative to said frame.
6. The instrument of claim 1, wherein said first jaw and said second jaw each normally extend in a direction generally perpendicular to the longitudinal axis of said frame.
7. The instrument of claim 1, wherein said biasing means comprises a first spring having a certain spring force and interconnecting said actuator and said frame; and including a second spring having a spring force less than said certain spring force for biasing said second jaw away from said first jaw.
8. The instrument of claim 1, wherein each of said first jaw and said second jaw includes a recess between said respective tip and said means coupling said second jaw to said frame.

9. An instrument for removing orthodontic brackets from teeth comprising:
   an elongated frame including a handle portion;
   a first jaw connected said frame and having a tip with a generally flat edge for gripping a side of an orthodontic bracket;
   a second jaw coupled to said frame and having a tip with a generally flat edge opposed to said edge of said first jaw for gripping an opposite side of the bracket;
   pivot means for selectively moving said second jaw about an axis and in a direction either toward or away from said first jaw,
   said first jaw and said second jaw each extending in a direction generally perpendicular to the longitudinal axis of said frame, and said first jaw, said second jaw and said handle each generally lying in respective reference planes which are perpendicular to said axis of pivotal movement.

10. The instrument of claim 9, wherein said respective reference planes are co-planer.